United States Patent [19]

Morris et al.

[11] Patent Number: 4,689,430

[45] Date of Patent: Aug. 25, 1987

[54] PROCESS FOR THE COPRODUCTION OF A DIALKYL OXALATE AND TERTIARY BUTANOL

[75] Inventors: George E. Morris, Egham; Gillian Wainhouse, Byfleet, both of England

[73] Assignee: The British Petroleum Company p.l.c., London, United Kingdom

[21] Appl. No.: 931,606

[22] Filed: Nov. 17, 1986

Related U.S. Application Data

[62] Division of Ser. No. 741,250, Jun. 4, 1985, Pat. No. 4,644,078.

[30] Foreign Application Priority Data

Jun. 14, 1984 [GB] United Kingdom ............... 8415150

[51] Int. Cl.$^4$ ............................................. C07C 67/36
[52] U.S. Cl. .................................... 560/204; 502/102; 560/190; 568/578; 568/876
[58] Field of Search ............... 560/204; 568/571, 578, 568/876; 502/102, 160, 165, 166, 167, 223, 225, 230, 326, 331

[56] References Cited

U.S. PATENT DOCUMENTS

| | | | |
|---|---|---|---|
| 2,862,973 | 12/1958 | Winkler et al. | 562/549 X |
| 3,987,115 | 10/1976 | Zajacek et al. | 568/570 X |
| 4,138,580 | 2/1979 | Umemura et al. | 560/81 |
| 4,160,107 | 7/1979 | Agnes et al. | 560/204 |
| 4,404,406 | 9/1983 | Lutz et al. | 568/571 |

*Primary Examiner*—Werren B. Lone
*Assistant Examiner*—Vera C. Clarke
*Attorney, Agent, or Firm*—Brooks Haidt Haffner & Delahunty

[57] ABSTRACT

A process for the production of a dialkyl carbonate, e.g. dimethyl carbonate, or a dialkyl oxalate, e.g. dimethyl oxalate, from butane, oxygen carbon monoxide and an alcohol is provided in a series of integrated process steps. In the case of a dialkyl oxalate, the product can be hydrogenated further to produce an ether of ethylene glycol.

10 Claims, No Drawings

PROCESS FOR THE COPRODUCTION OF A DIALKYL OXALATE AND TERTIARY BUTANOL

This is a division of application Ser. No. 741,250, filed June 4, 1985, now U.S. Pat. No. 4,644,078.

The present invention relates to a continuous process for the coproduction of tertiary butanol and either a dialkyl carbonate or a dialkyl oxalate from butane, oxygen, carbon monoxide and methanol in an integrated series of process steps.

Dialkyl carbonates, of which dimethyl carbonate is an example, are excellent solvents and have been used in the manufacture of cellulose nitrate and lacquers. They are also used as components in greases, lubricating oils and the preparation of polycarbonate resins by transesterification. A potentially more important use of dimethyl carbonate is as an additive to liquid hydrocarbon fuels such as gasoline. Recent research has shown that the addition of dimethyl carbonate to gasoline causes an increase in the octane number of the finished gasoline. Dimethyl carbonate may therefore be an alternative to lead compounds as an 'anti-knock' agent. Furthermore since it is burnt during combustion its degradation products are environmentally acceptable.

Our European patent application No. 0112172 has recently claimed a novel method of preparing dihydrocarbyl carbonates, in particularly dimethyl carbonate by the copper catalysed reaction of a primary or secondary alcohol, carbon monoxide and a dihydrocarbyl peroxide, for example di-tertiary butyl peroxide, at elevated temperature and pressure. During this reaction there is co-produced with the carbonate an alcohol derived from the hydrocarbyl group of the dihydrocarbyl peroxide. Thus, for example, if the dihydrocarbyl peroxide is di-tertiary butyl peroxide the alcohol coproduced is tertiary butanol.

Dialkyl oxalates, of which dimethyl oxalate is an example, also have industrial uses. These uses include applications in analysis and the dyestuff industry and include the use of oxalates as a bleaching agent for straw. A further potential use for dialkyl oxalates is in the production of ethylene glycol. Thus it is known that dialkyl oxalates can be hydrogenated to the dialkyl ethers of ethylene glycol which themselves can either be used or converted into ethylene glycol.

Our European patent application No. 0112171 claims a process for making dihydrocarbyl oxalates, in particular dimethyl oxalate, by the copper and palladium catalysed reaction of a primary or secondary alcohol, carbon monoxide and a dihydrocarbyl peroxide, for example di-tertiary butyl peroxide, at elevated temperature and pressure. During this reaction there is coproduced with the oxalate an alcohol derived from the hydrocarbyl groups of the dihydrocarbyl peroxide.

Comparison of the two processes described in these two patent applications show that the major difference between them is the catalyst used; thus for a dihydrocarbyl carbonate a copper catalyst is used while for a dihydrocarbyl oxalate a copper and palladium catalyst is required.

It is the purpose of the present invention to provide a process for the production of either a dialkyl carbonate or dialkyl oxalate, by a series of integrated steps from readily available starting materials and in particular, from butane gas, oxygen, carbon monoxide and an alcohol. As the two processes described above only differ in the catalyst used in the carbonylation stage, the same integrated process can be used for preparing either a dialkyl carbonate or a dialkyl oxalate by the correct choice of catalyst.

Accordingly, the present invention comprises a process for the coproduction of either a dialkyl carbonate or a dialkyl oxalate and tertiary butanol from butane, oxygen, an alcohol and carbon monoxide by an integrated series of steps which process comprises:
(1) in an isomerisation step isomerising the butane feed to a product rich in isobutane,
(2) in an oxidation step, oxidising the isobutane with oxygen to a mixture of tertiary butanol and tertiary butyl hydroperoxide,
(3) in a dehydration step, dehydrating the mixture of tertiary butanol and tertiary butyl hydroperoxide to produce di-tertiary butyl peroxide,
(4) in a carbonylation step reacting the di-tertiary butyl peroxide with the alcohol and carbon monoxide in the presence of either a copper catalyst or a copper promoted palladium catalyst to produce respectively either a dialkyl carbonate or a dialkyl oxalate and as co-product tertiary butanol,
(5) in one or more separation steps separating the products of step (4) from each other, any unreacted starting materials and the catalyst.

By dialkyl carbonate or dialkyl oxalate is meant a carbonate or oxalate ester in which the ester groups are derived from a $C_1$–$C_6$ alkyl alcohol. The alcohol may be either primary or secondary and can be, for example methanol, ethanol isopropanol, tertiary and the like. However, a preferred alcohol is methanol and preferred dialkyl carbonates or dialkyl oxalates are dimethyl carbonate or dimethyl oxalate.

Accordingly a preferred embodiment of the present invention comprises a process for the coproduction of either (i) dimethyl carbonate or dimethyl oxalate and (ii) tertiary butanol from butane, oxygen, methanol and carbon monoxide by an integrated series of steps which process comprises.:
(1) in an isomerisation step isomerising the butane feed to a product rich in isobutane,
(2) in an oxidation step, oxidising the isobutane with oxygen to a mixture of tertiary butanol and tertiary butyl hydroperoxide,
(3) in a dehydration step, dehydrating the mixture of tertiary butanol and tertiary butyl hydroperoxide to produce di-tertiary butyl peroxide.
(4) in a carbonylation step reacting the di-tertiary butyl peroxide with methanol and carbon monoxide in the presence of either a copper catalyst or a copper promoted palladium catalyst to produce either dimethyl carbonate or dimethyl oxalate and as co-product tertiary butanol,
(5) in one or more separation steps separating the products of step (4) from each other, any unreacted starting materials and the catalyst.

Unit 1, in which step (1) occurs, is fed with the butane feedstock and causes isomerisation of the feedstock to a product which is mainly isobutane. The butane feedstock can be pure normal butane or can be a mixture of normal and isobutane. There can also be present in the feedstock significant amounts, for example up to 10% by weight, of $C_1$–$C_3$ hydrocarbons. A preferred butane feedstock, however, is typically one containing approximately 70% by weight normal butane and 30% isobutane as might be obtained commercially.

The isomerisation step can be carried out by using, for example, the process described in our British Pat. Nos. 953187 and 953189.

The product from step (1) which comprises mainly isobutane together with small amounts of n-butane and traces of $C_3$ hydrocarbons is then fed to Unit 2 in which step (2), the oxidation of isobutane to a mixture of tertiary butanol and tertiary butyl hydroperoxide, is carried out. The oxidation of isobutane to a mixture of tertiary butanol and tertiary butyl hydroperoxide has been disclosed in for example U.S. Pat. No. 3,987,115 or U.S. Pat. No. 4,404,406 and is a commercially operated process. The products of the oxidation step are a mixture of tertiary butanol and tertiary butyl hydroperoxide, which are fed to Unit 3, and unreacted normal and isobutane which are recycled to the isomerisation stage. Oxygen or an oxygen containing gas e.g. air can be used.

In Unit 3, the dehydration stage, the mixture of tertiary butanol and tertiary butyl hydroperoxide is dehydrated with concentrated sulphuric acid to form di-tertiary butyl peroxide and water. The products of Unit 3, di-tertiary butyl peroxide and water, present as an aqueous solution of sulphuric acid, are immiscible and can conveniently be separated by decantation, the di-tertiary butyl peroxide layer being fed to Unit 4 for carbonylation and the aqueous layer containing sulphuric acid being fed to a concentrator Unit 6 prior to recycling to Unit 3. The dehydration step is typically carried out in the temperature range 20°–80° C. preferably 30°–60° C. and at a pressure of up to 150 psig. A typical dehydration process using sulphuric acid is described in U.S. Pat. No. 2,862,973.

The di-tertiary butyl peroxide produced in Unit 3 is next fed to Unit 4 along with the alcohol and carbon monoxide feedstock and the appropriate catalyst where step (4), the catalysed carbonylation of the alcohol to a dialkyl carbonate or a dialkyl oxalate occurs. In addition to the di-tertiary butyl peroxide, the alcohol, carbon monoxide and catalyst, Unit 4 is also fed with a solvent in which the carbonylation reaction occurs. The solvent provides a convenient means for adding the catalyst to the reactor and for recovering the catalyst in the separation stage. The solvent is thus conveniently one in which the catalyst is soluble. Examples of such solvents are given in European patent application Nos. 0112171 and 0112172 which also gives details of the conditions under which the unit is preferably operated. It will be appreciated that the optimum conditions for operating Unit 4 will depend on the dialkyl carbonate or dialkyl oxalate that is being made. Unit 4 may be a single reactor but, as the carbonylation reaction is highly exothermic, preferably consists of a series of two or more reactors of increasing temperature in order to moderate the reaction and reduce the amount of side products formed.

The liquid products of Unit 4, that is the alcohol, dialkyl carbonate or dialkyl oxalate and tertiary butanol, together with the catalyst and solvent are separated from any unreacted carbon monoxide and fed to Unit 5. The unreacted carbon monoxide is recycled to Unit 4 or may be vented.

Unit 5, in which step (5), the separation of products occurs, consists of two or more distillation columns. In the first column (Unit 5A) the reaction products are separated from the catalyst and its solvent; the catalyst and its solvent being recycled to Unit 4, optionally through a catalyst reactivation/purification unit (Unit 7). After the initial distillation the other three products may be separated if desired in one or more distillation columns (Unit 5B) and any excess alcohol recycled to Unit 4. The dialkyl carbonate or dialkyl oxalate and tertiary butanol can be recovered pure, or alternatively a mixed dialkyl carbonate or dialkyl oxalate and tertiary butanol stream can be produced.

If a dialkyl oxalate is produced by the above process this can either be recovered or fed to a hydrogenation unit (Unit 8) where it is hydrogenated to ethylene glycol and the alcohol. The dialkyl oxalate can be hydrogenated using for example a copper/silica catalyst at elevated temperature and pressure. Suitable catalysts and conditions are disclosed in European Pat. No. 0046983.

The tertiary butanol co-product may also be partially recycled to the dehydration Unit 3 for reaction with tertiary butyl hydroperoxide. This can be particularly useful when Unit 2 is operated under conditions such that there is produced more tertiary butyl hydroperoxide than tertiary butanol. In such a case, the recycled tertiary butanol allows the feed to Unit 3 to be adjusted to a molar ratio of tertiary butyl hydroperoxide to tertiary butanol of 1:1 thereby satisfying the stoichiometry of the dehydration step.

The preferred embodiment of the invention is essentially the same as described previously except that the alcohol fed to unit 4 is methanol and the dialkyl carbonate or dialkyl oxalate produced is dimethyl carbonate or dimethyl oxalate. The dimethyl oxalate can be hydrogenated in Unit 8 to produce ethylene glycol and methanol.

The invention described will now be illustrated by reference to the following example.

EXAMPLE

A butane stream, typically consisting of 70% normal butane and 30% isobutane, was fed to Unit 1 and converted to a mixture containing greater than 98% isobutane. The isobutane rich product was fed to Unit 2 along with an oxygen stream the reactor being maintained at a temperature in the range 133°–138° C. and at 36 bars under conditions which converted 50% of the isobutane fed into oxygenated products (molar ratio of tertiary butanol: tertiary butyl hydroperoxide=1:1). The unreacted isobutane was separated and recycled.

In the dehydration stage (Unit 3) a mixture comprising 72 g of tertiary butyl hydroperoxide and 78 g of tertiary butanol was cooled to 5° C. 70% sulphuric acid (130 g) was added to the mixture and the mixture vigorously agitated. During this time, the temperature of the reaction was maintained below 15° C. After a typical reactor residence time of 10 minutes the product mixture was removed from the reaction zone and allowed to warm to 40° C. During this time two phases formed. The upper phase (109 g) was separated by decantation and fed to Unit 4. The lower, aqueous sulphuric acid was fed to the concentrator prior to recycling to Unit 3.

The first carbonylation reactor of Unit 4 was charged with 109 g of di-tertiary butyl peroxide, 47.8 g of methanol, 3.7 g of cuprous chloride and 21 g of 2,6-dimethyl pyridine. Carbon monoxide was also introduced so as to correspond to a room temperature pressure of 43 bars. The first reactor was held at a temperature of 83° C. The reaction so produced was passed through a series of reactors of increasing temperature at rates which allowed the reaction to be carefully controlled. The last reactor was maintained at 125° C. During the total reaction time 8½ hours, carbon monoxide was consumed and it was necessary at certain points to introduce further carbon monoxide to maintain pressure. The product mixture leaving the final reactor contained 69.6 of dimethyl carbonate.

The product mixture leaving Unit 4 was fed to Unit 5A. In Unit 5 the mixture was heated to 60° C. under reduced pressure and the volatile components removed. The involatile residue consisting of the copper catalyst and 2,6-dimethyl pyridine was removed from the bottom of Unit 5 and recycled to Unit 4.

The volatile products of Unit 5A were condensed and fed to Unit 5B where the remaining components were separated.

We claim:

1. A process for the coproduction of a dialkyloxalate and tertiary butanol from butane, oxygen, an alcohol and carbon monoxide by an integrated series of steps which process comprises:
   (1) in an isomerisation step isomerising the butane feed to a product rich in isobutane,
   (2) in an oxidation step, oxidising the isobutane with oxygen to a mixture of tertiary butanol and tertiary butyl hydroperoxide,
   (3) in a dehydration step, dehydrating the mixture of tertiary butanol and tertiary butyl hydroperoxide to produce di-tertiary butyl peroxide,
   (4) in a carbonylation step reacting the di-tertiary butyl peroxide with the alcohol and carbon monoxide in the presence of a copper promoted palladium catalyst to produce a dialkyl oxalate and as co-product tertiary butanol,
   (5) in one or more separation steps separating the products of step (4) from each other, any unreacted starting materials and the catalyst.

2. A process as claimed in claim 1 wherein the alcohol is a $C_1$–$C_6$ alky alcohol and the dialkyl oxalate is a $C_1$–$C_6$ dialkyl oxalate.

3. A process as claimed in claim 2 wherein the alcohol is selected from ethanol, isopropanol and tertiary butanol and the appropriate dialkyl oxalate is produced.

4. A process as claimed in claim 2 wherein the alcohol is methanol and the dialkyl oxalate is dimethyl oxalate.

5. A process as claimed in claim 1 wherein a dialkyl oxalate is produced in step (4) and the process further comprises step (6) in which the dialkyl oxalate is hydrogenated to the alcohol and ethylene glycol.

6. A process as claimed in claim 5 wherein the dialkyl oxalate is dimethyl oxalate and wherein the dimethyl oxalate is hydrogenated to methanol and ethylene glycol.

7. A process as claimed in claim 1 wherein the tertiary butanol co-product of step (4) is recycled to step (3).

8. A process as claimed in claim 1 wherein step (3) is carried out in the presence of sulphuric acid as a dehydrating agent.

9. A process as claimed in claim 1 wherein the catalyst from step (1) is purified and reactivated in a catalyst recovery step.

10. A process as claimed in claim 1 wherein step (4) is carried out in a series of two or more reactors of increasing temperature.

* * * * *